(12) United States Patent
Leet et al.

(10) Patent No.: US 8,263,644 B2
(45) Date of Patent: Sep. 11, 2012

(54) CYTOTOXIC XANTHONE COMPOUNDS

(75) Inventors: John E. Leet, Madison, CT (US); Craig R. Fairchild, Yardley, PA (US); Stephen W. Mamber, Annandale, VA (US); Xiaohong Liu, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 200 days.

(21) Appl. No.: 12/677,926

(22) PCT Filed: Sep. 11, 2008

(86) PCT No.: PCT/US2008/075916
§ 371 (c)(1),
(2), (4) Date: Mar. 12, 2010

(87) PCT Pub. No.: WO2009/036106
PCT Pub. Date: Mar. 19, 2009

(65) Prior Publication Data
US 2010/0311826 A1    Dec. 9, 2010

Related U.S. Application Data

(60) Provisional application No. 60/971,983, filed on Sep. 13, 2007.

(51) Int. Cl.
*A01N 43/16* (2006.01)
*A61K 31/35* (2006.01)
*C07D 311/78* (2006.01)
*C07D 311/94* (2006.01)
*C07D 311/82* (2006.01)

(52) U.S. Cl. ......... 514/453; 514/454; 549/383; 549/392

(58) Field of Classification Search .................. 514/453, 514/454; 549/383, 392
See application file for complete search history.

(56) References Cited

U.S. PATENT DOCUMENTS

| 5,041,424 A | 8/1991 | Saulnier et al. |
| 7,244,760 B2 | 7/2007 | Hurley et al. |
| 2003/0120093 A1 | 6/2003 | Hurley et al. |
| 2006/0084698 A1 | 4/2006 | Hurley et al. |

FOREIGN PATENT DOCUMENTS

| JP | 10 203977 | 8/1998 |
| WO | WO02/094836 | 11/2002 |
| WO | WO 2006/023445 | 3/2006 |

OTHER PUBLICATIONS

Tanaka et al., "Prenylated Benzophenones and Xanthones From Hypericum Scabrum"; Journal of Natural Products, 2004, vol. 67, pp. 1870-1875.
Leet et al., "Cytotoxic Xanthones From Psorospermum Molluscum From the Madagascar Rain Forest", Journal of Natural Products, 2008, vol. 78, pp. 460-463.

*Primary Examiner* — Sreeni Padmanabhan
*Assistant Examiner* — Samira Jean-Louis

(57) ABSTRACT

The present invention relates to xanthone compounds isolated from the plant *Psorospermum molluscum* Hochr. (Clusiaceae), a Madagascar plant, which are potent cytotoxic agents.

8 Claims, No Drawings

CYTOTOXIC XANTHONE COMPOUNDS

CROSS REFERENCE TO RELATED APPLICATIONS

The present application is a 371 application of PCT/US2008/075916 filed Sep. 11, 2008, which claims priority benefit of U.S. provisional application Ser. No. 60/971,983, filed Sep. 13, 2007, each of which are incorporated by reference herein.

FIELD OF THE INVENTION

The present invention relates to xanthone compounds isolated from the plant *Psorospermum molluscum* Hochr. (Clusiaceae), a Madagascar plant.

DESCRIPTION OF THE INVENTION

Nature remarkably has served as an abundant source of highly potent cytotoxic agents that have been explored and developed as successful chemotherapeutic agents. For example, naturally-produced or derived chemotherapeutic agents include paclitaxel (Taxol®) and docetaxel (Taxotere®), plant alkaloids derived from the bark of the Pacific yew tree *Taxus brevifolia* and the needles of the European yew tree *Taxus baccata*, respectively; etoposide (VP-16, I) and teniposide (VM-26, II), which are semisythetic glycodside derivatives of podophyllotoxin, an antimitotic and topoisomerase II agent derived from the mandrake plant; the vinca alkaloids—vinblastine, vincrisitne, and vinorelbine—naturally occurring or semisynthetic derivatives of the perwinkle plant; the epothilones and their analogs, derived from the bacterial strain *Sorangisum cellulosum*, which class of compounds include the recently approved drug Ixempra®, an aza-epothilone B analog now being marketed for treatment of breast cancer; as well as various other therapeutically-active polyketides produced by nature including erythromycin, FK-506, FK-520, megalomicin, rapaymcin, rebeccamycin, ansamycin, ambruticin, laulimides, migrastatin, mycolactone, and discodermolides, to name a few.

The compound psorospermin is a cytotoxic dihydrofuranoxanthone isolated from the roots and stembark of the African plant *psorospermum febrifugum*, having the structure:

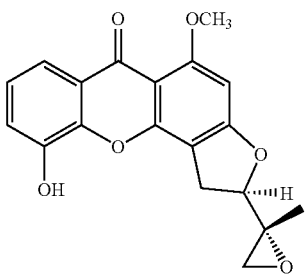

Also isolated from *psorospermum febrifugum* is a chlorohydrin counterpart to psorospermin, having the formula:

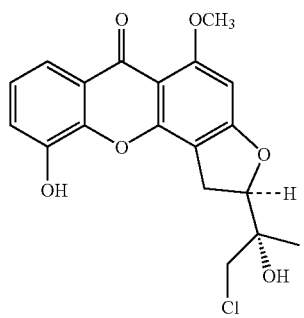

The psorospermins are potent DNA alkylating antitumor agents; psorospermin has been shown to exhibit significant activity in vitro against various tumor cell lines and in vivo again p388 mouse leukemia. See, e.g., U.S. Pat. No. 7,244,760, incorporated herein by reference, and WO 02/094836. It is believed that the anti-tumor activity is related to its interaction with the DNA topoisomerase II complex. See also Kwok, Y., Hurley, L. H.; *J. Biol. Chem.*, 1998, 273, 33020-33026; Kwok, Y., Zeng, Q., Hurley, L. H.; *Proc. Natl. Acad. Sci. USA*, 1998, 95, 13531-13536; and Kupchan, S. M., Streelman, D. R., Sneden, A. T.; *J. Nat. Prod.*, 1980, 43, 296-301; Habib, A. M., Ho, D. K., Masuda, S., McCloud, T.; Reddy, K. S., Aboushoer, M., McKensie, A., Byrn, S. R., Chang, C.-J., Cassady, J. M.; *J. Org. Chem.*, 1987, 52, 412-418.

Psorospermin reportedly is no longer readily available from its natural plant source in Africa, and in view of its potent anti-tumor activity, others have pursued alternative methods for preparing psorospermin. See, e.g., U.S. Pat. No. 7,244,760, WO 02/094836, US2006/0084698A1; US 2003/0120093A1; EP 1395596A2; WO2006/023445A2; incorporated herein by reference.

Topoisomerases are vital nuclear enzymes which function to resolve topological dilemmas in DNA, such as overwinding, underwinding and catenation, which normally arise during replication, transcription and perhaps other DNA processes. These enzymes allow DNA to relax by forming enzyme-bridged strand breaks that act as transient gates or pivotal points for the passage of other DNA strands. Topoisomerase-targeting drugs appear to interfere with this breakage-reunion reaction of DNA topoisomerases. In the presence of topoisomerase active agents an aborted reaction intermediate, termed a 'cleavable complex', accumulates and results in replication/transcription arrest, which ultimately leads to cell death. *Cancer Chemother. Pharmacol* 1994, 34 (suppl), S41-S45, discusses topoisomerase I active compounds that are in clinical studies and have been found to be effective clinical antitumor agents. Indolo[2,3-a]carbazole derivatives related to the Rebeccamycin class, such as NB-506, are disclosed (EP Appl. 0 545 195 B1 and 0,602,597 A2; *Cancer Research* 1993, 53, 490-494; ibid 1995, 55, 1310-1315) and claimed to exhibit antitumor activity. These derivatives have been reported to be non-selective, exhibiting additional biological effects, such as DNA intercalation (*Cancer Research* 1995, 55, 1310), tyrosine kinase activity (Molecular Pharmacol. 1999, 56, 185-195) and topoisomerase II activity (*Proc. AACR* 1997, 38, 75).

DNA topoisomerase II is an enzyme which is essential to the life of eukaryotic cells. It changes the topology of the DNA by transient double-stranded cleavage of a DNA double helix, through which it passes another DNA helix. In addition to the biological advantage of this enzyme, there is a pharmacological advantage, since it is the preferred target of many antitumor agents (Corbett and Osheroff, Chem. Res. Toxicol., 6, 585 (1993)). For example, etoposide, referenced above, is a widely used antineoplastic agent having a mechanism of action due to its ability to inhibit the enzyme DNA-topoisomerase II by stabilizing a cleavable enzyme DNA complex in which the DNA is cleaved and covalently linked to the enzyme [Ross, W. Rowe, T.; Glisson, B.; Yalowch J.; and Liu, L. Role of Topoisomerase II in Mediating Podophyllotoxin-Induced DNA Cleavage, Cancer Res.; 1984, 44: 5857-5860].

DETAILED DISCLOSURE

The present application is directed to certain xanthane compounds isolated from the plant *Psorospermum molluscum* Hochr. (Clusiaceae), a Madagascar plant; and to pharmaceutical compositions containing the compounds and methods of treating cancer or other proliferative conditions using the compounds.

According to one aspect of the invention, there is provided isolated compounds having the formulae:

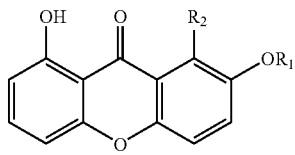

wherein $R_1$ is hydrogen and $R_2$ is —C(H)═C(CH$_3$)CH$_2$OH, or $R_1$ and $R_2$ are taken together to form a group

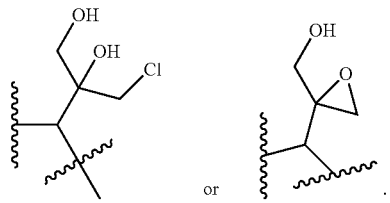

According to another aspect of the invention, there are provided isolated compounds having the formulae (1), (4) or (5), below:

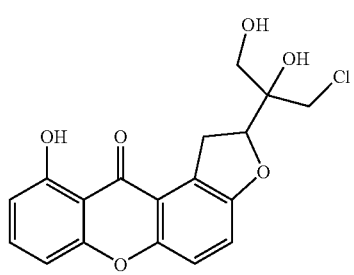

(1)

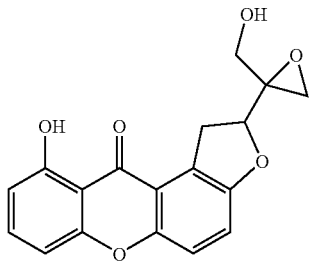

(4)

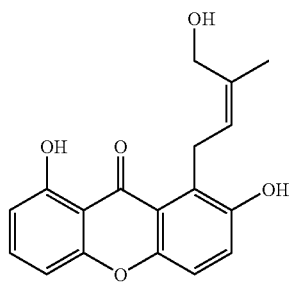

(5)

According to another aspect of the invention, there is provided compounds of the above formulae (1), (4) or (5), that are substantially purified, i.e., having a degree of purity of greater than 90%, more preferably greater than 95%, even more preferably greater than 97%.

According to another aspect of the invention, there is provided use. Use of a compound in preparing a medicament for treating cancer, comprising administering a therapeutically effective amount of a compound according to formula (I), (4) or (5) to a patient.

These compounds (1, 4) have potent cytotoxicity in a 6-cell line panel (mean IC$_{50}$ ranges from 0.2 μg/ml to 4 μg/ml). In particular there was a clear in vitro cytotoxicity observed against ABAE cells (bovine endothelial cell line, 0.03 μg/ml).

The compounds were isolated from the plant *Psorospermum molluscum* Hochr. (Clusiaceae) as dichloromethane-methanol extracts derived from the wood, stems and roots.

The crude extracts as received were subjected to a modified "Kupchan" liquid-liquid partitioning sequence, (Kupchan, S. M., Britton, R. W., Ziegler, M. F., Sigel, C. W.; *J. Org. Chem.*, 1973, 38, 178-179.), followed by gel partition chromatography (Sephadex LH-20) and/or Silica gel vacuum liquid chromatography. The fractionation was guided initially by TLC-bioautography using the *Escherichia coli* SOS chromotest assay. ((a) Quillardet, P.; Huisman, O.; D'Ari, R.; Hofnung, M. *Proc. Natl. Acad. Sci. U.S.A.* 1982, 79, 5971-5975. (b) Mamber, S. W.; Okasinski, W. G.; Pinter, C. D.; Tunac, J. B. *Mutat. Res.*, 1986, 171, 83-90.). More precise localization of the peak of SOS activity was later made possible using HPLC biogram methodology. ((a) Fura, A.; Shu, Y.-Z.; Zhu, M.; Hanson, R. L.; Roongta, V.; Humphreys, W. G. *J. Med. Chem.* 2004, 47, 4339-4351. (b) Hook, D. J., More, C. F., Yacobucci, J. J., Dubay, G., O'Connor, S.; J. Chromatogr., 1987, 385, 99-108.). In this manner, analytical HPLC was used to further fractionate the SOS-active sample into 96-deep-well plates. The fraction collection utilized a time-based protocol, resulting in a direct relationship between a well's position in the plate and a corresponding area on the HPLC chromatogram. Subsequent bioassay of all fractions using the SOS chromotest revealed activity correlated with an extremely minor cluster of peaks (i.e. barely detectable by UV) in the chromatogram. Final purification of the SOS-active complex was achieved after repeated reversed phase HPLC. In this manner, fractionation of *P. molluscum* wood stem extract yielded a new SOS-active compound, psoroxanthin chlorohydrin (1). Also identified in the extract by NMR, UV, and MS were the known 2-hydroxyxanthone (2) and 1,7-dihydroxyxanthone (3). (2-Hydroxyxanthone: (a) Lins Mesquita, A. A., De Barros Correa, D., Gottlieb, O., R., Taveira Magalhaes, M.; *Anal. Chim. Acta.*, 1968, 42, 311-323. (b) Afzal, M., Al-Hassan, J. M., Al-Masad, F. N.; *Heterocycles*, 1979, 12, 269-299; 1,7 Dihydroxyxanthone: UV (a) Chow, Y. L., Quon, H. H.; *Phytochemistry*, 1968, 7, 1871-1874. (b) Locksley, H. D., Moore, I., Scheinmann, F.; *J. Chem. Soc.* (C), 1966, 430-432. NMR (c) Westerman, P. W., Gunasekera, S. P., Uvais, M., Sultanbawa, S., Kazlauskas, R.; *Org. Magn. Reson.* 1977, 9, 631-636.). Likewise, fractionation of *P. molluscum* root extract yielded a second new SOS-active compound, psoroxanthin (4), plus a new prenylated xanthone, 8-(4'-hydroxyprenyl)-1,7-dihydroxyxanthone (5), and again 2-hydroxyxanthone (2).

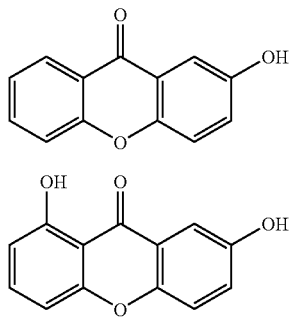

Compound 1 was isolated from the wood stem extract as a yellow amorphous solid (4.8 mg). The MS spectrum obtained in positive mode utilizing electrospray ionization (+ve ESI) indicated that 1 was monochlorinated with a molecular weight of 362 Da. Its molecular formula was established as $C_{18}H_{15}O_6Cl$ by high resolution accurate mass analysis (HR +ve ESI) ([M+H]+ at m/z 363.0634, calcd 363.0635), indicating 11 degrees of unsaturation in the molecule. Its UV spectrum ($\lambda$max 243, 264, 292, 325, 396 nm) was highly similar to that of 1,7-dihydroxyxanthone, a known xanthone found in this extract. (1,7 Dihydroxyxanthone: UV (a) Chow, Y. L., Quon, H. H.; *Phytochemistry*, 1968, 7, 1871-1874. (b) Locksley, H. D., Moore, I., Scheinmann, F.; *J. Chem. Soc.* (C), 1966, 430-432. NMR (c) Westerman, P. W., Gunasekera, S. P., Uvais, M., Sultanbawa, S., Kazlauskas, R.; *Org. Magn. Reson.* 1977, 9, 631-636.). The $^1$H-NMR spectrum (DMSO-$d_6$) featured a hydrogen-bonded hydroxyl proton singlet ($\delta$ 12.59), 5 ortho-coupled aromatic signals (1 proton each) at $\delta$ 7.71 (t, J=8.3 Hz), 7.44 (d, J=9.0 Hz), 7.37 (d, J=9.0 Hz), 7.03 (d, J=8.0 Hz), and 6.78 (d, J=8.5 Hz), a methine triplet resonance at $\delta$5.04 (J=9.3 Hz), 2 methylene signals, $\delta$ 3.84, (2H, s), 3.76 (2H, dd, J=9.0, 3.0 Hz), and a methylene pair $\delta$ 3.53, 3.46 (J=11.0 Hz). In the $^{13}$C spectrum, 13 of the 18 signals were consistent with a 1,7-dioxyxanthone moiety within the molecule. The additional 5 signals were attributed to an isoprenoid unit and these included 3 methylene carbons ($\delta$ 61.2, 46.4, 31.1), one methine ($\delta$ 85.2) and one quaternary carbon ($\delta$ 74.7). Long-range proton-carbon correlations (HMBC) were observed between one of the methylene pairs, H1' ($\delta$ 3.75) of the isoprenoid unit to C7 ($\delta$ 156.0), C8 ($\delta$ 125.5) and C8a ($\delta$ 117.0), thus establishing linkage of the isoprenoid unit to C8 of the 1,7-dioxyxanthone system. Furthermore, two 3-bond proton-carbon correlations between H2' ($\delta$ 5.04) and C7 ($\delta$ 156.0), C8 ($\delta$ 125.5) support the presence of a dihydrofuran ring fused at C7, C8 of the xanthone ring system (Scheme 1). The structural assignment of compound 1 is corroborated by HR +ve ESI MS/MS data, where a key loss of 109 Da, i.e. [$C_3H_6O_2Cl$], was observed (Scheme 2), resulting in a product ion at m/z 253.0499 ([M-$C_3H_6O_2Cl$+H]$^+$, calcd 253.0501). Thus compound 1, named 3' 4' deoxy-4'-chloropsoroxanthin-(3',5'-diol), is essentially a highly substituted isoprenoid (prenylated) derivative of 1,7 dihydroxyxanthone.

Fig 1: HMBC Correlations for (1)

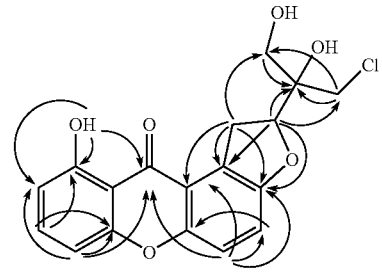

Fig 2: MS/MS Fragmentation of (1)

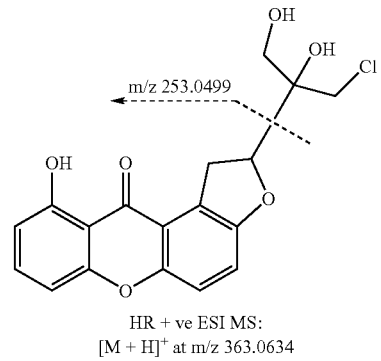

HR + ve ESI MS:
[M + H]$^+$ at m/z 363.0634

The second, highly potent SOS-active xanthone (4) was isolated by repeated HPLC of the enriched SOS-active fraction from the root extract in extremely low yield (<0.1 mg). The +ve ESI MS spectrum indicated that 4 has a molecular weight of 326 Da. Its molecular formula was established as $C_{18}H_{14}O_6$ by HR +ve ESI ([M+H]$^+$ at m/z 327.0867, calcd 327.0869), indicating 12 degrees of unsaturation in the molecule. Its HPLC-UV spectrum ($\lambda_{max}$ 242, 265, 292, 325, 396 nm) was essentially identical to that of 1, indicative of a structural analog having the 1,7 dioxyxanthone chromophore. (1,7 Dihydroxyxanthone: UV (a) Chow, Y. L., Quon, H. H.; *Phytochemistry*, 1968, 7, 1871-1874. (b) Locksley, H. D., Moore, I., Scheinmann, F.; *J. Chem. Soc.* (C), 1966, 430-432. NMR (c) Westerman, P. W., Gunasekera, S. P., Uvais, M., Sultanbawa, S., Kazlauskas, R.; *Org. Magn. Reson.* 1977, 9, 631-636.). To achieve a superior NMR spectrum free of background impurity and solvent signals, the sample was analyzed in a LC-NMR experiment. In this manner, the $^1$H-NMR spectrum of the separated peak (H$_2$O—CH$_3$CN 7:3 mobile phase) featured 5 ortho-coupled aromatic signals (1 proton each), as observed in 1, at $\delta$ 7.62 (t, J=8.4 Hz), 7.32 (d, J=8.4 Hz), 7.23 (d, J=9.0 Hz), 6.94 (d, J=8.4 Hz), and 6.71 (J=8.4 Hz), a methine triplet resonance at $\delta$ 5.08 (dd, J=10.2, 7.8 Hz), a methylene doublet, $\delta$ 3.71, (2H, J=7.2 Hz), and a methylene pair: ($\delta$ 3.85, 1H, dd, J=18.0, 10.2 Hz; 3.63, 1H, dd, J=17.2, 7.2 Hz). A second methylene pair ($\delta$ 2.98, 1H, d, J=4.8 Hz; 2.85, 1H, d, J=4.2 Hz) was highly indicative of an epoxide moiety in the molecule. The structural assignment of compound 4 is corroborated by HR +ve ESI MS/MS data, where a key loss of 73 Da, i.e. [$C_3H_5O_2$], was observed, resulting in a product ion at m/z 253.0500 ([$M-C_3H_5O_2+H$]$^+$, calcd 253.0501).

In the course of HPLC isolation of psoroxanthin (4), a later eluting peak (5) was collected (0.8 mg). The +ve ESI MS spectrum indicated that 5 has a molecular weight of 312 Da. Its molecular formula was established as $C_{18}H_{16}O_5$ by HR +ve ESI ([$M+H$]$^+$ at m/z 313.1088, calcd 313.1076), indicating 11 degrees of unsaturation in the molecule. Its UV spectrum ($\lambda_{max}$ 240, 264, 292, 320, 390 nm) was again nearly identical to that of 1 and 4, indicative of a structural analog having the 1,7 dioxyxanthone chromophore. (1,7 Dihydroxyxanthone: UV (a) Chow, Y. L., Quon, H. H.; *Phytochemistry*, 1968, 7, 1871-1874. (b) Locksley, H. D., Moore, I., Scheinmann, F.; *J. Chem. Soc. (C)*, 1966, 430-432. NMR (c) Westerman, P. W., Gunasekera, S. P., Uvais, M., Sultanbawa, S., Kazlauskas, R.; *Org. Magn. Reson.* 1977, 9, 631-636.). As in the case of 1, long-range proton-carbon correlations were observed between the C1' methylene protons ($\delta$ 4.03) of the isoprenoid side chain unit to C7 ($\delta$ 152.3), C8 ($\delta$ 127.1) and C8a ($\delta$ 119.1), again establishing linkage of this unit to C8 of the xanthone system. A 4'-hydroxyprenyl moiety (i.e. (Z)-2-methylbut-2-en-1-ol) was deduced from COSY, HMQC, and HMBC NMR spectra. In addition, the Z-configuration was supported from a 1D NOESY experiment, where irradiation of H2' ($\delta$ 5.22) led to NOE enhancement of the methyl group signal H5' ($\delta$ 1.62). The structure of 5 is thus 8-(4'-hydroxyprenyl)-1,7-dihydroxyxanthone.

EXAMPLES

General Experimental Procedures. NMR spectra were obtained on a Bruker DRX 500 MHz spectrometer, equipped with a 5-mm TXI cryoprobe. Proton and carbon chemical shifts are reported in ppm relative to DMSO at $\delta_H$ 2.49 and $\delta_C$ 39.6. LC-NMR on an enriched psoroxanthin (4) sample was conducted with a Varian Inova 600 MHz instrument, using a YMC ODS-AQ (C18) column, 4.6×150 mm, 3µ and mobile phase water-acetonitrile 7:3, isocratic, 1.2 ml/min flow rate. Low-resolution MS and MS/MS measurements were performed by +ve ESI on a Thermo Scientific Finnigan SSQ7000 (single quadrupole MS), TSQ7000 (triple quadrupole MS), or LCQ Classic (ion trap MS). High-resolution MS data were determined by HR +ve ESI on a Thermo Scientific Finnigan MAT900 (magnetic sector MS, polypropylene glycol reference) or Orbitrap (hybrid ion trap-FTICR MS). IR spectra were recorded with a Perkin-Elmer System 2000 FT-IR instrument (thin film-NaCl). UV spectra were obtained using a Hewlett-Packard 8452A diode array spectrophotometer. Sephadex LH-20 (Pharmacia Biotech) and LiChroprep Si 60, 25-40 µm (EM Separations) were used for column chromatography. HPLC(C18) conditions: Analytical: Agilent HP-1100, Waters corp. X-Terra 5 µl (C18) column, 4.6×150 mm; mobile phase: 0.01 N potassium phosphate buffer pH 3.5-acetonitrile gradient, flow rate 1.2 ml/min. UV 254 nm (Hook, D. J., More, C. F., Yacobucci, J. J., Dubay, G., O'Connor, S.; *J. Chromatogr.*, 1987, 385, 99-108.) Preparative: Beckman System Gold workstation, YMC ODS-A 5µ (C18) column, 20×100 mm. For TLC biogram (SOS) analyses, Silica gel plates (Analtech, 0.25 mm) with chloroform-methanol mixtures (i.e. 95:5 v/v) as the mobile phase were used. For HPLC biogram (SOS) analyses, fractions were collected into Beckman 96-deepwell plates using a Gilson 215 liquid handler and dried under nitrogen stream prior to bioassay. Methods for the *E. coli* SOS chromotest and tumor cell cytotoxicity assays have been described previously. (Quillardet, P.; Huisman, O.; D'Ari, R.; Hoihung, M. *Proc. Natl. Acad. Sci. U.S.A.* 1982, 79, 5971-5975. Mamber, S. W.; Okasinski, W. G.; Pinter, C. D.; Tunac, J. B. *Mutat. Res.*, 1986, 171, 83-90; Cory, A. H., Owen, T. C., Barltrop, J. A., Cory, J. G.; *Cancer Commun.* 1991, 3, 207-212.)

Plant Material. The plant *Psorospermum molluscum* Hochr. (Clusiaceae) was collected by botanists from the Missouri Botanical Gardens (St. Louis, Mo.) under the direction of Chris Birkenshaw, from an area of Madagascar known as Fianarantsoa at a height of 1200 meters. Voucher samples (collector numbers Q66V4221 (roots), Q66V4223 (wood stems) are held at Missouri Botanical Gardens and at the National Herbarium, Smithsonian Institution, Washington, D.C.

Extract Preparation. The plant parts (roots, wood stems) were separated and air-dried, ground in a ball mill, and extracted at room temperature by soaking overnight in dichloromethane-methanol 1:1 (v/v), followed by methanol. The extracts from each plant part were pooled, dried under vacuum, and stored at −20° C.

Isolation. The crude extract from wood stems (1.0 g) was dissolved in methanol-water 9:1 (100 ml) and extracted 3 times with equal volumes of n-hexane. The aqueous methanol layer was diluted with 20 ml water to give a methanol-water 3:1 ratio, and extracted 3 times with equal volumes of toluene. The aqueous methanol phase was further diluted with 18 ml water to give a methanol-water 65:35 ratio, and then extracted 3 times with pre-saturated chloroform. TLC bioautography of all fractions using the SOS chromotest revealed prominent zones of inhibition in the toluene extract (71 mg). The remaining available extract (8 g) was processed as above, giving 706 mg additional toluene extract. The toluene extracts were pooled and subjected to silica gel VLC. The extract was preadsorbed onto 2 g of Merck LiChroprep silica gel 60 (25-40 µm) and applied to a 2.5×15 cm fritted filter funnel packed with 15 g of silica gel. Elution using house vacuum was carried out with hexane, followed by hexane-chloroform 3:1, 1:1, 1:3, chloroform, chloroform-methanol 98:2 (2 times), 95:5, 90:10 v/v (all 100 ml fractions). TLC bioautography revealed strong SOS activity in the initial chloroform-methanol 98:2 fraction (198 mg). This fraction (75 mg portion) was subjected to repeated preparative C18 HPLC, using a mobile phase of 0.01% aq. trifluoroacetic acid (TFA)-acetonitrile 60:40 with a concave gradient to acetonitrile over a period of 20 minutes, flow rate 20 ml/min, UV detection 254 nm. This afforded the new psoroxanthin chlorohydrin 1 (10 min peak, 4.8 mg), as well as 2-hydroxyxanthone 2 (4.6 min peak, 6.6 mg) and 1,7-dihydroxyxanthone 3 (7.8 min peak, 22.4 mg).

The crude extract from roots (11 g) was dissolved in methanol-water 9:1 (100 ml) and extracted 3 times with equal volumes of n-hexane. The aqueous methanol layer was diluted with 38 ml water to give a methanol-water 65:35 ratio, and extracted 3 times with equal volumes of pre-saturated chloroform. The SOS active chloroform extract (1.47 g) was subjected to Sephadex LH-20 chromatography using chloroform-methanol 1:1 eluant. The SOS active fractions were pooled (422 mg) and further chromatographed by silica gel VLC as previously described. The peak of SOS activity was in the chloroform fraction (11.9 mg) and this was subjected to preparative HPLC as previously described, affording 2-hydroxyxanthone (2) (4.4 min peak, 2.6 mg), and 8-(4'-hydroxyprenyl)-1,7-dihydroxyxanthone (5) (10.5 min peak, 0.8 mg). The peak of SOS activity was detected in a minor, broad peak (7.9-9.1 min, 0.2 mg). Final purification of this SOS active peak in the course of an LC-NMR experiment afforded psoroxanthin (4) (>0.1 mg). Known xanthones 2, 3 were identified by comparison of their UV, NMR, MS spectra with published data. (2-Hydroxyxanthone: (a) Lins Mesquita, A. A., De Barros Correa, D., Gottlieb, O., R., Taveira Magalhaes, M.; *Anal. Chim. Acta.*, 1968, 42, 311-323. (b) Afzal, M., Al-Hassan, J. M., Al-Masad, F. N.; *Heterocycles,* 1979, 12, 269-299; 1,7 Dihydroxyxanthone: UV (a) Chow, Y. L., Quon, H. H.; *Phytochemistry,* 1968, 7, 1871-1874. (b) Locksley, H. D., Moore, I., Scheinmann, F.; *J. Chem. Soc.* (*C*), 1966, 430-432. NMR (c) Westerman, P. W., Gunasekera, S. P., Uvais, M., Sultanbawa, S., Kazlauskas, R.; *Org. Magn. Reson.* 1977, 9, 631-636.).

Example 1

Psoroxanthin chlorohydrin (3',4'-deoxy-4' chloropsoroxanthin-3',5'-diol) (1): yellow solid; UV (MeOH) $\lambda_{max}$ 243 ($\epsilon$ 23200), 264 (29810), 292 (4400), 325 (3400), 396 (4600); IR $\nu_{max}$ 3445, 2936, 1642, 1605, 1585, 1478, 1462, 1365, 1337, 1278, 1219, 1056, 1038, 978, 816, 759 cm$^{-1}$; HR +ve ESI MS, $C_{18}H_{15}O_6Cl$, [M+H]$^+$ at m/z 363.0634, calcd 363.0635.

NMR Data for Psoroxanthin chlorohydrin (1) (500 MHz, DMSO-d$_6$)

| Position | $^{13}C$ ppm | $^1H$ ppm (mult, J (Hz)) | HMBC ($^{13}C$-$^1H$ correlations) |
|---|---|---|---|
| C1 | 160.8 | | 12.59, 7.71 |
| C1-OH | | 12.59 (1H, s) | |
| C2 | 109.5 | 6.78 (1H, d, (8.5)) | 12.59, 7.03 |
| C3 | 137.2 | 7.71 (1H, d, (8.3)) | |
| C4 | 107.0 | 7.03 (1H, d, (8.0)) | |
| C4a | 155.9 | | 7.71, 7.03 |
| C4b | 150.2 | | 7.37 |
| C5 | 117.0 | 7.44 (1H, d, (9.0)) | |
| C6 | 117.3 | 7.37 (1H, d, (9.0)) | 7.44 |
| C7 | 156.0 | | 7.44, 7.37w, 5.04, 3.75 |
| C8 | 125.5 | | 7.37, 5.04, 3.75 |
| C8a | 117.0 | | 7.44, 3.75 |
| C9 | 182.7 | | 12.59w, 7.44w, 7.03w |
| C9a | 108.3 | | 6.78 |
| C1' | 31.1 | 3.75 (2H, dd, (9.0, 3.0)) | 5.04 |
| C2' | 85.2 | 5.04 (1H, t, 9.3) | 3.84, 3.75, 3.53, 3.46 |
| C3' | 74.7 | | 5.04, 3.84, 3.75, 3.53, 3.46 |
| C4' | 46.4 | 3.84 (2H, s) | 5.04 |
| C5' | 61.2 | 3.46 (1H, d, 11.0) | 3.84 |
| | | 3.53 (1H, d, 11.0) | | w = weak coupling

Example 2

Psoroxanthin (4): yellow solid; HPLC-UV (aq. CH$_3$CN) $\lambda_{max}$ 242, 265, 292, 325, 396 nm; HR +ve ESI MS, $C_{18}H_{14}O_6$, [M+H]$^+$ at m/z 327.0867, calcd 327.0869.

NMR Data for Psoroxanthin (4)

| Position | $^{13}C^a$ ppm (DMSO) | $^1H$ ppm (mult, J (Hz)) (DMSO) | $^1H$ ppm (mult, J (Hz)) (LC-NMR shifts) |
|---|---|---|---|
| C2 | 110.5 | 6.72 (1H, d, (8.2)) | 6.71 (1H, d, (8.4)) |
| C3 | 138.3 | 7.64 (1H, t, (8.3)) | 7.62 (1H, t, (8.4)) |
| C4 | 108.0 | 6.96 (1H, d, (8.4)) | 6.94 (1H, d, (8.4)) |
| C5 | 118.4 | 7.38 (1H, d, (8.7)) | 7.32 (1H, d, (8.4)) |
| C6 | 118.0 | 7.30 (1H, d, (8.8) | 7.23 (1H, d, (9.0) |
| C1' | 33.8 | 3.63 (1H, m) | 3.63 (1H, dd, (17.2, 7.2)) |
| | | 3.85 (1H, m) | 3.85 (1H, dd, (18.0, 10.2)) |
| C2' C3' | 83.8 | 5.10 (1H, dd, (10.2, 7.8)) | 5.08 (1H, dd, (10.2, 7.8)) |
| C4' | 48.0 | 2.74 (1H, d, (5.0)) | 2.98 (1H, d, (4.8)) |
| | | 2.86 (1H, d, (5.0)) | 2.85 (1H, d, (4.2)) |
| C5' | 61.6 | 3.60 (1H, m) | 3.71 (2H, d, (7.2)) |
| | | 3.57 (1H, m) | |

Example 3

8-(4'-hydroxyprenyl)-1,7-dihydroxyxanthone (5): yellow solid; UV (MeOH) $\lambda_{max}$ 240 ($\epsilon$ 17500), 264 (21110), 292 (4500), 320 (2800), 390 (3600); IR $\nu_{max}$ 3389, 2966, 1683, 1645, 1603, 1486, 1463, 1384, 1291, 1265, 1225, 1153, 1057, 981, 818, 758 cm$^{-1}$; HR +ve ESI MS, $C_{18}H_{16}O_5$, [M+H]$^+$ at m/z 313.1088, calcd 313.1076.

NMR Data for 8-(4'-hydroxyprenyl)-1,7-dihydroxyxanthone (5) (600 MHz, DMSO-d$_6$)

| Position | $^{13}C$ ppm | $^1H$ ppm (mult, J (Hz)) | HMBC ($^{13}C$-$^1H$ correlations) |
|---|---|---|---|
| C1 | 155.6 | | 6.94, 7.63, 6.71 |
| C1-OH | | 12.96 (1H, s) | |
| C2 | 110.1 | 6.71 (1H, d, (8.0)) | 6.94 |
| C3 | 137.4 | 7.63 (1H, t, (8.2) | |
| C4 | 107.3 | 6.94 (1H, d, (8.5)) | 6.71 |
| C4a | 162.0 | | 6.71, 7.63, 6.94 |
| C4b | 151.7 | | 7.36 |
| C5 | 117.1 | 7.36 (1H, m) | |
| C6 | 124.7 | 7.36 (1H, m) | |
| C7 | 152.3 | | 4.03 |
| C8 | 127.1 | | 7.36, 4.03 |
| C8a | 119.1 | | 7.36, 4.03 |
| C9 | 185.0 | | 6.94, 6.71, 7.36 |
| C9a | 109.5 | | |
| C1' | 25.3 | 4.03 (2H, d, (6.9)) | 5.22 |
| C2' | 124.6 | 5.22 (1H, t, 6.9) | 4.03, 4.17, 1.62 |
| C3' | 136.0 | | 4.17, 4.03, 1.62 |
| C4' | 60.5 | 4.17 (2H, s) | 5.22, 1.62 |
| C5' | 27.0 | 1.62 (3H, s) | 5.22, 4.17 |

Biological Evaluation

The SOS active compounds 1 and 4 were evaluated for in vitro cytotoxicity in a variety of tumor cell lines. In particular, 1 showed selectivity against bovine endothelial cells (ABAE). The results are illustrated in the table below.

CYTOTOXICITIES OF XANTHONES 1 AND 4 (IC$_{50}$ μM) IN VARIOUS CELL LINES

| | Example 1 | Example 4 |
|---|---|---|
| A2780 | 0.042 | 0.33 |
| HCT-116 | 0.068 | 1.0 |
| ABAE | 0.004 | 0.102 |
| SKBR3 | 2.0 | Not Tested |

Utility

In view of the compounds cytotoxic activity as described above, it is expected they are useful as anti-cancer agents for treatment of various cancers or proliferative diseases, including, for example, pancreatic cancer, prostate cancer, myeloma, ovarian cancer, or breast cancer. (See, e.g., US 2003/0120093) In addition, as with the psorospermins and etoposide and in view of their topoisomerase II activities, it is expected the compounds will be useful for treatment of not only the above cancers but also in treatment of leukemias and lymphoma including non-Hodgkin's lymphoma (see, e.g., U.S. Pat. No. 7,244,760), as well as testicular, small cell lung, thyroid, bladder, brain, non-lymphocytic leukemia, and Hodgkin's disease (see, e.g., U.S. Pat. No. 5,041,424).

The isolated compounds of the invention may form salts or solvates which are also within the scope of this invention. Reference to a compound of the specific formulae herein is understood to include reference to salts and solvates thereof, unless otherwise indicated. The term "salt(s)", as employed herein, denotes acidic and/or basic salts formed with inorganic and/or organic acids and bases. In addition, when a compound of formula (I) contains both a basic moiety, such as but not limited to a pyridinyl imidazolyl, amine or guanidinyl and an acidic moiety such as but not limited to a carboxylic acid, zwitterions may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the specific formulae may be formed, for example, by reacting a compound of formula (I) with an amount of acid or base, such as an equivalent amount, in a medium such as one in which the salt precipitates or in an aqueous medium followed by lyophilization.

The compounds of the invention that contain a basic moiety, such as but not limited to an amine, a guanidinyl group, or a pyridyl or imidazolyl ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3 phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of the invention that contain an acidic moiety, such as but not limited to a carboxylic acid, may form salts with a variety of organic and inorganic bases. Exemplary basic salts include ammonium salts; alkali metal salts such as sodium, lithium, and potassium salts; alkaline earth metal salts such as calcium and magnesium salts; salts with organic bases (for example, organic amines) such as benzathines, dicyclohexylamines, hydrabamines (formed with N,N-bis (dehydroabietyl)ethylenediamine), N-methyl-D-glucamines, N-methyl-D-glycamides, t-butyl amines; and salts with amino acids such as arginine, lysine, and the like. Basic nitrogen-containing groups may be quaternized with agents such as lower alkyl halides (e.g. methyl, ethyl, propyl, and butyl chlorides, bromides, and iodides), dialkyl sulfates (e.g. dimethyl, diethyl, dibutyl, and diamyl sulfates), long chain halides (e.g. decyl, lauryl, myristyl, and stearyl chlorides, bromides, and iodides), aralkyl halides (e.g. benzyl and phenethyl bromides), and others.

Solvates of the compounds of the invention are also contemplated herein. Solvates of the compounds of the invention include, for example, hydrates.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. Racemic forms can be resolved by physical methods, such as, for example, fractional crystallization, separation or crystallization of diastereomeric derivatives, or separation by chiral column chromatography. Individual optical isomers can be obtained from stereospecific processes, wherein starting materials and/or intermediates are selected having a stereochemistry corresponding with that desired for the end products, and the stereochemistry is maintained throughout the reactions, and/or the isomers can be obtained from racemates by any suitable method, including without limitation, conventional methods, such as, for example, salt formation with an optically active acid followed by crystallization.

All configurational isomers of the compounds of the present invention are contemplated, either in admixture, or in pure or substantially pure form. As can be appreciated, the preferred configuration can be a function of the particular compound and the activity desired. Configurational isomers may be prepared by the processes described herein, which may be stereoselective. In other words, a desired stereochemistry for the final compounds can be achieved by using starting materials having the corresponding desired stereochemistry, and then maintaining the stereoselectivity throughout the process of preparation. Alternatively, the compounds may be prepared as racemates or diastereomers, and then the desired stereochemistry may be achieved via separation of configurational isomers which can be achieved by any suitable method known in the field, e.g., such as column chromatography.

The compounds of the present invention can be administered for any of the uses described herein by any suitable means, for example, parenterally, such as by subcutaneous, intravenous, intramuscular, or intrasternal injection or infusion techniques (e.g., as sterile injectable aqueous or non-aqueous solutions or suspensions), and/or in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution (0.9% Sodium Chloride Injection [Normal Saline] or 5% Dextrose Injection), or other suitable dispersing or wetting and suspending agents, including synthetic mono- or diglycerides, and fatty acids. Pharmaceutically acceptable compositions and/or methods of administering compounds of the invention may include use of co-solvents including, but not limited to ethanol, N,N dimethylacetamide, propylene glycol, glycerol and polyethylene glycols, e.g., polyethylene glycol 300 and/ or polyethylene glycol 400, may comprise use of surfactants (pharmaceutically-acceptable surface active agent that may be used to increase a compound's spreading or wetting properties by reducing its surface tension), including without limitation, CREMOPHOR®, polysorbate 80, polysorbate 20, poloxamer, pyrrolidones such as N-alkylpyrrolidone (e.g., N-methylpyrrolidone) and/or polyvinylpyrrolidone; may also comprise use of one or more "buffers" (e.g., an ingredient which imparts an ability to resist change in the effective acidity or alkalinity of a medium upon the addition of increments of an acid or base), including, without limitation, sodium phosphate, sodium citrate, diethanolamine, triethanolamine, L-arginine, L-lysine, L histidine, L-alanine, glycine, sodium carbonate, tromethamine (a/k/a tris[hydroxymethyl]aminomethane or Tris), and/or mixtures thereof.

The effective amount of the compound of the present invention can be determined by one of ordinary skill in the art, and includes exemplary dosage amounts for an adult human of from about 0.01-10 mg/kg of body weight of active compound per day, which can be administered in a single dose or in the form of individual divided doses, such as from 1 to 4 times per day. A preferred range includes a dosage of about 0.02 to 5 mg/kg of body weight, with a range of about 0.05-0.3, being most preferred. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to microtubule-stabilization associated conditions.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. An isolated compound having the formula,

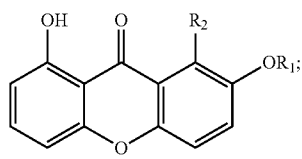

wherein $R_1$ and $R_2$ are taken together to form a group

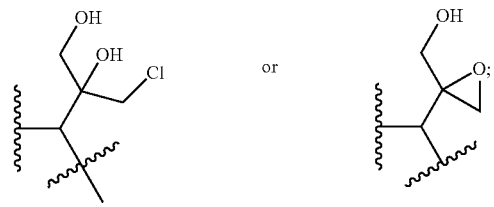

or a pharmaceutically-acceptable salt thereof.

2. An isolated compound of claim 1, having the formula:

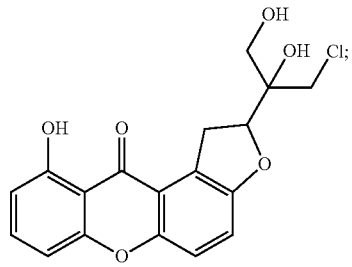

or a pharmaceutically-acceptable salt thereof.

3. An isolated compound of claim 1, having the formula:

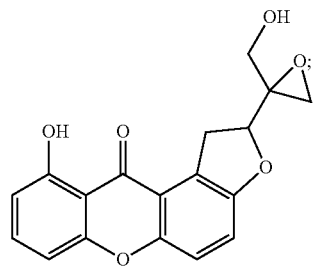

or a pharmaceutically-acceptable salt thereof.

4. An isolated compound having the following formula:

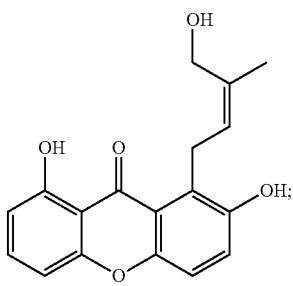

or a pharmaceutically-acceptable salt thereof.

5. A pharmaceutical composition, comprising a compound according to claim 1, or salt thereof, and a pharmaceutically acceptable carrier or diluent.

6. A method of treating colon cancer, breast cancer, or ovarian cancer in a patient, comprising administering a therapeutically effective amount of a pharmaceutical composition according to claim 5 to the patient.

7. A pharmaceutical composition comprising a compound according to claim 4, or salt thereof, and a pharmaceutically acceptable carrier or diluent.

8. A method of treating colon cancer, breast cancer, or ovarian cancer in a patient, comprising administering a therapeutically effective amount of a pharmaceutical composition according to claim 7 to the patient.

* * * * *